United States Patent [19]
Pritchard et al.

[11] Patent Number: 5,762,770
[45] Date of Patent: Jun. 9, 1998

[54] ELECTROCHEMICAL BIOSENSOR TEST STRIP

[75] Inventors: G. John Pritchard, Salem, Mass.; Joseph E. Bateson, Carmel, Ind.; Brian S. Hill, Indianapolis, Ind.; Brian A. Heald, Fishers, Ind.; Scott E. Hubbard, Fountaintown, Ind.

[73] Assignee: Boehringer Mannheim Corporation, Indianapolis, Ind.

[21] Appl. No.: 496,939

[22] Filed: Jun. 30, 1995

Related U.S. Application Data

[63] Continuation-in-part of Ser. No. 198,407, Feb. 22, 1994, Pat. No. 5,508,171.

[51] Int. Cl.⁶ .................... C12Q 1/54; G01N 27/327
[52] U.S. Cl. .................... 204/403; 205/777.5; 435/4; 435/11; 435/14
[58] Field of Search ............... 204/403, 416, 204/418, 419; 435/817, 4, 11, 14, 288, 291; 205/777.5

[56] References Cited

U.S. PATENT DOCUMENTS

| | | | |
|---|---|---|---|
| 4,842,712 | 6/1989 | Seshimoto et al. | 204/418 |
| 4,897,173 | 1/1990 | Nankai et al. | 204/403 |
| 5,288,636 | 2/1994 | Pollmann et al. | 435/288 |
| 5,385,846 | 1/1995 | Kuhn et al. | 204/403 |
| 5,395,504 | 3/1995 | Saurer et al. | 204/403 |

*Primary Examiner*—T. Tung
*Attorney, Agent, or Firm*—D. Michael Young; Max J. Kenemore; Brent A. Harris

[57] ABSTRACT

An electrochemical biosensor test strip that has a minimum volume blood sample requirement of about 9 microliters. The test strip has working and counter electrodes that are substantially the same size and made of the same electrically conducting material placed on a first insulating substrate. Overlaying the electrodes is a second insulating substrate, which includes a cutout portion that forms a reagent well. The cutout portion exposes a smaller area of the counter electrode than the working electrode. A reagent for analysis of an analyte substantially covers the exposed areas of working and counter electrodes in the reagent well. Overlaying the reagent well and affixed to the second insulating substrate is a spreading mesh that is impregnated with a surfactant. The small cutout portion of 4 millimeters by 4.2 millimeters, small mesh of 6 millimeters by 5.8 millimeters, and small amount of reagent, 4 microliters before drying, allow the test strip to analyze a whole blood sample of about 9 microliters.

10 Claims, 3 Drawing Sheets

ELECTROCHEMICAL BIOSENSOR TEST STRIP

CROSS-REFERENCES TO RELATED APPLICATIONS

This application is a continuation-in-part of U.S. patent application Ser. No. 08/198,407, filed Feb. 22, 1994, now U.S. Pat. No. 5,508,171, the disclosure of which is hereby incorporated by reference.

FIELD OF THE INVENTION

This invention relates generally to the determination of the concentration of analytes in fluids and more specifically to an amperometric biosensor for use in such determination.

BACKGROUND OF THE INVENTION

Biosensors are not new. Their use in the determination of concentrations of various analytes in fluids is also known.

Nankai et al., WO 86/07632, published Dec. 31, 1986, discloses an amperometric biosensor system in which a fluid containing glucose is contacted with glucose oxidase and potassium ferricyanide. The glucose is oxidized and the ferricyanide is reduced to ferrocyanide. (This reaction is catalyzed by glucose oxidase.) After two minutes, an electrical potential is applied and a current caused by the re-oxidation of the ferrocyanide to ferricyanide is obtained. The current value, obtained a few seconds after the potential is applied, correlates to the concentration of glucose in the fluid.

Because Nankai et al. discloses a method in which the reaction of glucose and ferricyanide may run to completion prior to the application of an electrical potential, this method is referred to as the "end-point" method of amperometric determination.

Nankai et al. discloses a system, wherein the glucose oxidase and potassium ferricyanide are held on a nonwoven nylon mesh. The mesh is positioned so that it is in contact with a working electrode, a counter electrode and a reference electrode. The total surface area of the counter and reference electrodes is twice that of the working electrode.

Wogoman, EP 0 206 218, published Dec. 30, 1986 discloses a biosensor having two electrodes, the electrodes being made of different electrically conducting materials. For example, the anode is formed from an anode material, such as platinum, and the cathode is formed from a cathode material, such as silver. The anode is coated with an enzyme. In a preferred embodiment, the coated electrode is covered with an elastomer that is permeable to glucose.

Pottgen et al., WO 89/08713, published Sep. 21, 1989, discloses the use of a two electrode biosensor, wherein the electrodes are made of the same noble metal, but one of the electrodes (referred to as a pseudoreference electrode) is larger than the other (working) electrode.

Recently, Pollmann et al., U.S. Pat. No. 5,288,636, issued Feb. 22, 1994, disclosed an electrochemical biosensor test strip that includes working and counter electrodes of substantially the same size and made of the same electrically conducting materials. The Pollmann et al. test strip includes a reagent well that will accommodate a testing sample of human whole blood from about 10 to about 70 microliters. However, below about 13 microliters, errors in the measurement of an analyte, such as glucose, from a whole blood sample may result (low dosing errors). Generally, the low dosing error is manifested as an understated measurement of the analyte, or no measurement of the analyte by the meter used in conjunction with the test strip. Low dosing errors are a particular concern for infants and elderly persons who often have difficulty in expressing a reasonably sized blood drop for testing upon pricking their finger with a lancet.

Accordingly, it is highly desirable to design a test strip that requires a minimum volume of blood for the testing of an analyte, such as blood glucose.

SUMMARY OF THE INVENTION

The invention is an electrochemical biosensor test strip that has a lower minimum volume blood sample requirement than prior art strips of similar construction. The present inventive test strip has a smaller reagent well and smaller spreading mesh than similar prior art strips. Further, the reagent well is positioned differently than in similar prior art test strips. The minimum blood volume sample requirement for the new strip is about 9 microliters.

The smaller sample volume requirement means fewer low sample volume dosing errors result when measuring an analyte, such as glucose, from a whole blood sample. This result is especially important for those persons, such as infants and the elderly, who have difficulty expressing a reasonably sized drop of blood by pricking their finger with a lancet. Also, with the present inventive strip it is easier for the meter, which collects current measurements and correlates those measurements to a concentration of analyte from a sample, to discriminate low sample volume dosing errors. Further, the smaller reagent well requires less reagent per biosensor strip, thereby increasing the production volume for mass production of biosensor test strips.

Additionally, when the spreading mesh is affixed to the test strip by an adhesive tape, the tape includes a hole that exposes the reagent well and spreading mesh, and further includes air vents on opposing sides of the hole. These air vents reduce the occurrence of air bubbles trapped in the reagent well when a sample is being tested. Air bubbles can produce testing errors.

DESCRIPTION OF THE PREFERRED EMBODIMENT

Figure 1:
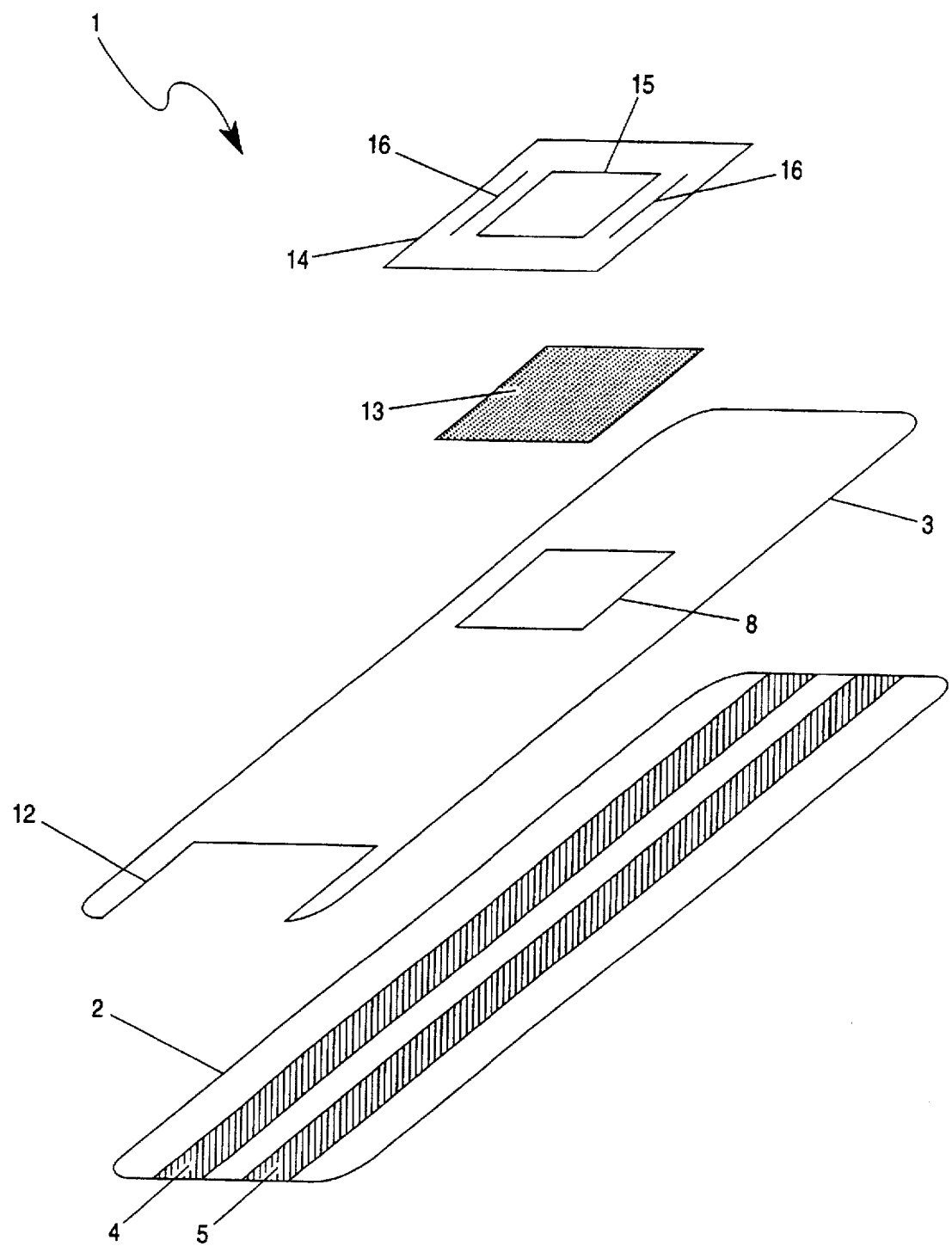
FIG. 1 is an exploded view of the present inventive biosensor test strip.
Figure 2:
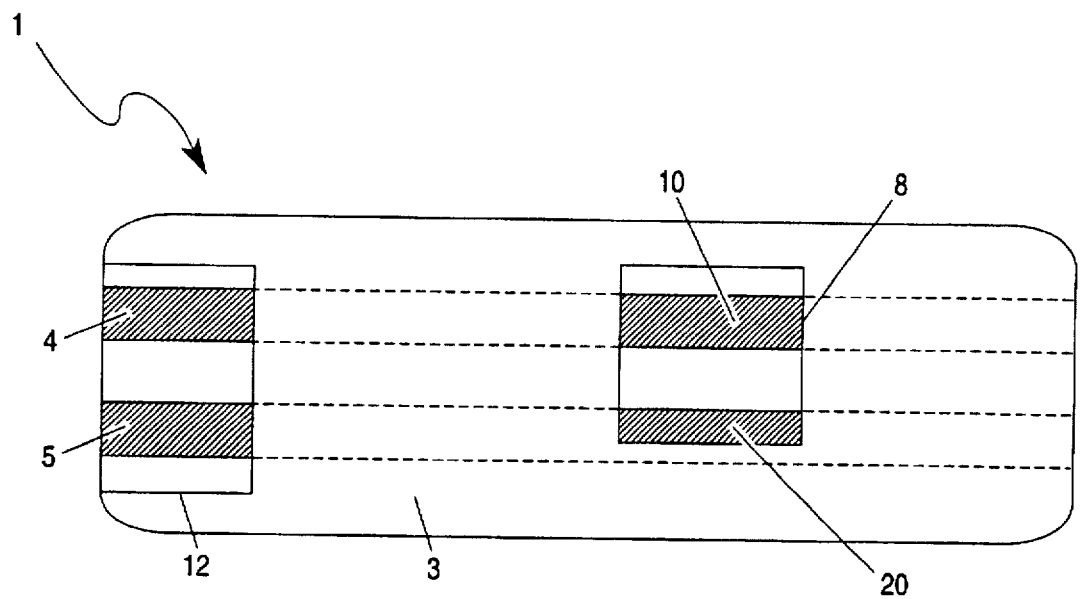
FIG. 2 is a top view of the biosensor test strip without the reagent, spreading mesh, and adhesive tape with air vents.

The present inventive biosensor test strip is similar to the preferred embodiment of the test strip described in Pollmann et al., U.S. Pat. No. 5,288,636, issued Feb. 22, 1994, the disclosure of which is hereby incorporated by reference. However, the Pollmann et al. strip has a construction such that too many low dosing errors result when whole blood samples below about 13 microliters are tested for blood glucose.

In the present inventive test strip, reagent well 9 (FIG. 4) has been reduced in size over the Pollmann et al. reagent well and repositioned so that a smaller surface area of the counter electrode 5 than the working electrode 4 is exposed by cutout portion 8, which forms reagent well 9. (FIGS. 1–4) Mesh 13, which is a spreading mesh, is also reduced in size over the Pollmann et al. mesh. (FIGS. 1, 3, 4) These changes in strip architecture result in a test strip that can accurately measure an analyte, such as glucose, from a minimum whole blood sample of about 9 microliters.

Referring specifically to FIGS. 1 through 4, there is shown the presently preferred embodiment of the inventive biosensor test strip.

Test strip 1 comprises first and second electrically insulating layers 2 and 3, respectively. Any useful insulating material will be suitable. Typically, plastics, such as vinyl polymers and polyimides provide the electrical and structural properties which are desired. Preferably, these layers are Melinex 329, 7 mil.

The biosensor test strip shown in FIGS. 1 through 4 is intended to be mass produced from rolls of material, necessitating the selection of a material which is sufficiently flexible for roll processing and at the same time sufficiently stiff to give a useful stiffness to the finished biosensor test strip.

Layers 2 and 3 may be of any useful thickness. In a preferred embodiment, layers 2 and 3 are about 7 mil thick.

Working electrode 4 and counter electrode 5 are preferably deposited on a backing of insulator material 7, such as polyimide, to reduce the possibility of tearing the electrode before it is affixed to layer 2. Working electrode 4 and counter electrode 5 are substantially the same size and are made of the same electrically conducting material. Examples of electrically conducting materials that may be used are palladium, platinum, gold, silver, carbon, titanium, and copper. Noble metals are preferred because they provide a more constant, reproducible electrode surface area. Palladium is particularly preferred because it is one of the more difficult noble metals to oxidize and because it is a relatively inexpensive noble metal. Silver is not preferred because it is more readily oxidized by air than the other noble metals listed above. Preferably, electrodes 4 and 5 are about 0.1 micron thick and backing 7 is about 25 microns thick (commercially available from Courtaulds Performance Films in California and Southwall Technologies, Inc.).

Electrodes 4 and 5 must be sufficiently separated so that the electrochemical events at one electrode do not interfere with the electrochemical events at the other electrode. The preferred distance between electrodes 4 and 5 is about 1.2 millimeters.

In the preferred embodiment, electrodes 4 and 5, affixed to backing 7, are unspooled from reels and attached to layer 2 by the use of hot melt adhesive (not shown). Electrodes 4 and 5 also preferably extend from one end of layer 2 to the other end in parallel configuration.

Insulating layer 3 is fixed on top of layer 2 and electrodes 4 and 5 by the use of hot melt adhesive (not shown). Layer 3 includes cutout portion 8, which defines reagent well 9. Both the size and the position of cutout portion 8 are critical to the invention. Cutout portion 8 must be sufficiently small and must be sufficiently positioned such that in combination with the spreading mesh, described below, a minimum whole blood sample volume of about 9 microliters may be accurately analyzed by the test strip. The preferred size of cutout portion 8 is 4 millimeters by 4.2 millimeters.

In the preferred embodiment, the 4 mm side of cutout portion 8 runs parallel to the long side of the test strip shown in FIGS. 1–4. Importantly, cutout portion 8 is positioned over electrodes 4 and 5 such that a smaller surface area of counter electrode 5 than working electrode 4 is exposed. Preferably, the exposed surface area of working electrode 4 is twice as large as the exposed surface area of counter electrode 5. Surprisingly, offsetting cutout portion 8 to expose a smaller surface area for the counter electrode than the working electrode does not adversely affect measurement of an analyte from a sample being measured. In this preferred embodiment, electrodes 4 and 5 are 1.5 mm in width.

Biosensor test strip 1 may be accompanied by a power source (not shown) in a electrical connection with the working and counter electrodes and a current measuring meter (not shown) which is also in a electrical connection with the working and counter electrodes.

Biosensor reagent 11 (FIG. 4) is placed in well 9 so that it covers substantially all of exposed surfaces 10 and 20 of working electrode 4 and counter 5, respectively. (FIGS. 2–4) An example of a reagent that may be used in the biosensor test strip of the present invention is a reagent for measuring glucose from a whole blood sample.

A protocol for making a glucose reagent utilizing the enzyme glucose oxidase and ferricyanide as the oxidized form of the redox mediator is as follows:

Step 1—Prepare 1 liter (in a volumetric flask) of a buffer/NATROSOL mixture by adding 1.2000 grams (g) NATROSOL-250 M to 0.740M aqueous potassium phosphate buffer (including 80.062 g monobasic potassium phosphate and 26.423 g dibasic potassium phosphate) at pH 6.25. Allow the NATROSOL to stir and swell for 3 hours.

Step 2—Prepare an AVICEL mixture by stirring 14.0000 g AVICEL RC-591 F and 504.7750 g water for 20 minutes.

Step 3—Prepare a TRITON mixture by adding 0.5000 g TRITON X-100 to 514.6000 g of the buffer/NATROSOL mixture and stir for 15 minutes.

Step 4—While stirring, add the total TRITON mixture dropwise with an addition funnel or buret to the total AVICEL mixture. Once addition is complete, continue stirring overnight.

Step 5—To the mixture resulting from Step 4, add, while stirring, 98.7750 g potassium ferricyanide. (Add a little potassium ferricyanide at a time to allow the potassium ferricyanide to dissolve as added.)

Step 6—Stir the resulting mixture of Step 5 for 20 minutes.

Step 7—Adjust the pH of the mixture resulting from Step 6 to 6.25 by adding potassium hydroxide.

Step 8—To the resulting mixture of Step 7, add 9.1533 g glucose oxidase (218.50 tetramethyl benzidine units per milligram (mg) from Biozyme) and stir at least 20 minutes.

Step 9—To the resulting mixture of Step 8, add 20 g potassium glutamate and stir at least 20 minutes.

Step 10—Filter the resulting mixture of Step 9 through a 100 micron sieve bag to remove any AVICEL clumping. The filtrate is the resulting reagent composition (reagent 11), which is added to reagent well 9 and is then dried at about 50° C. for about 3 minutes.

In the preferred embodiment for glucose determination, 4 microliters of reagent made by the above-stated protocol is added to well 9 formed by cutout 8. This amount of reagent 11 will substantially cover surface areas 10 and 20 of the electrodes 4 and 5 (FIG. 2) and will also contain a sufficient amount of ferricyanide, and a sufficient amount of enzyme (glucose oxidase) to catalyze the oxidation of glucose (from a sample of human whole blood) and the reduction of ferricyanide to completion, as defined herein, within about 20 seconds. (Prior to adding the reagent to well 9, it is preferable to treat well 9 with a 600 Watt corona arc, gapped at 1/40,000 inch on a processing line travelling at 4 meters per minute, to make well 9 more hydrophilic, thereby allowing the reagent to spread more evenly in the well.)

Another glucose reagent that may be formulated includes 300 millimolar potassium ferricyanide, 250 millimolar potassium phosphate buffer, 14 grams microcrystalline cellulose (AVICEL RC-591 F) per liter of reagent, 0.6 grams hydroxyethylcellulose (NATROSOL-250 M) per liter of reagent, 0.5 grams Triton X-100 surfactant per liter of reagent, 37 millimolar sodium succinate, and 1.57 million tetramethyl benzidine units of glucose oxidase per liter of reagent. Sodium hydroxide (6 Normal solution) is used to titrate this reagent to a pH of 6.6. This reagent may be formulated by the same protocol described above, but amounts of components should be adjusted and components substituted (sodium succinate for potassium glutamate and sodium hydroxide for potassium hydroxide) to achieve the component concentrations stated above. Drying of this reagent in reagent well 9 typically results in a loss of enzyme activity of about 30–35%.

After drying reagent 11, a spreading mesh 13, which has been impregnated with a surfactant, is placed over cutout portion 8 and is affixed to second electrical insulator 3. Speading mesh 13 is preferably a polyester monofilament mesh from ZBF (Zurich Bolting Cloth Mfg. Co. Ltd., R üschlikon, Switzerland). The spreading mesh is preferably dipped in a solution of 0.8% (wt.:vol.) dioctylsodium sulfosuccinate (DONS) in a solution of 50:50 (vol.:vol.) methanol:water, and then dried. Spreading mesh 13 must be small enough such that in combination with the size of cutout portion 8 and placement of cutout portion 8 the biosensor strip will accurately measure analyte from a minimum whole blood sample of about 9 microliters. The preferable dimensions of spreading mesh 13 are 6 mm×5.8 mm. In the most preferred biosensor strip, the 6 mm side of the mesh is parallel to the long side of the strip shown in FIGS. 1–4.

Figure 3:
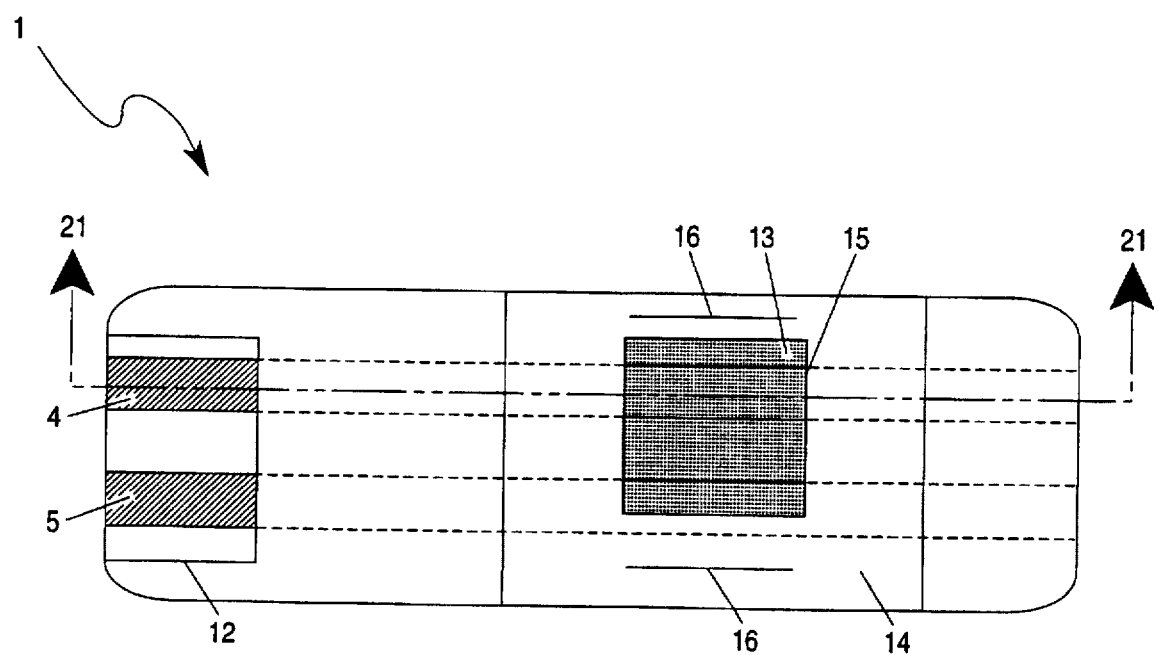
FIG. 3 is a top view of the fully constructed, preferred biosensor test strip.
Figure 4:
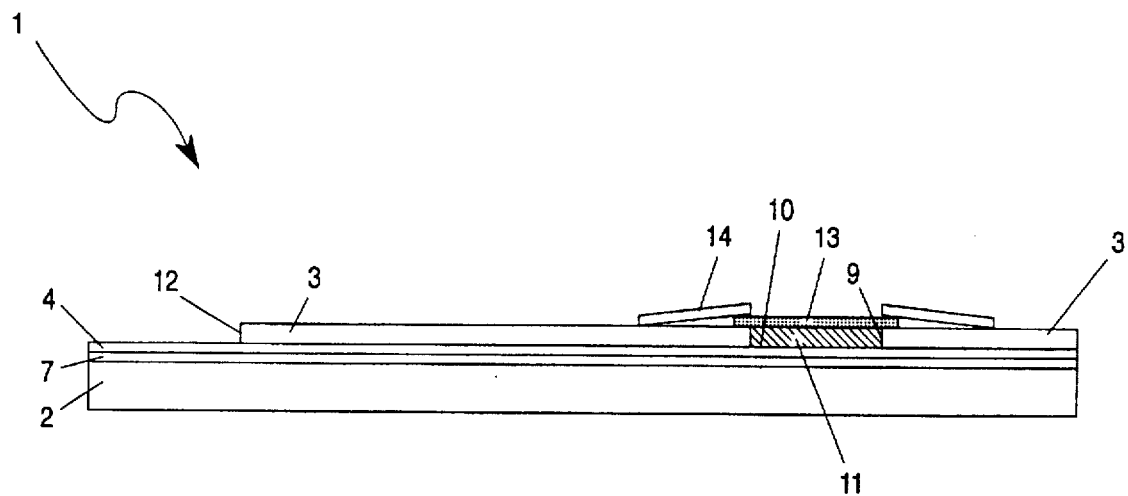
FIG. 4 is a cross-sectional view of the biosensor of FIG. 3 along lines 21—21.

Preferably, spreading mesh 13 is affixed to adhesive tape 14, which includes hole 15. (FIGS. 1, 3, 4) Adhesive tape 14 is preferably made of polyester with an adhesive backing. (Available from Tapemark, Medical Products Division, 223 E. Marie Ave., St. Paul, Minn. 55118) Adhesive tape 14 is preferably dyed maroon and hole 15 provides a target area for application of a sample to be analyzed by the biosensor. Hole 15 exposes at least a portion of spreading mesh 13 and cutout portion 8, and preferably exposes substantially all of cutout portion 8. Tape 14 preferably includes slits 16, as shown in FIGS. 1 and 3, located on opposing sides of hole 15. (Two slits 16 are shown in FIGS. 1 and 3, but one slit may be sufficient.) Slits 16 constitute air vents, which reduce the occurrence of air bubbles trapped in the reagent well upon the addition of a sample such whole blood to the reagent well. Reducing the occurrence of air bubbles trapped in reagent well 9 results in fewer testing errors.

After drying the reagent and affixing the spreading mesh, the roll-formed biosensors are separated by die punching to form discrete biosensors, which are used in conjunction with 1) a power source in electrical connection with the working and counter electrodes and capable of supplying an electrical potential difference between the working and counter electrodes sufficient to cause diffusion limited electrooxidation of the reduced form of the redox mediator at the surface of the working electrode, and 2) a meter in electrical connection with the working and counter electrodes and capable of measuring the diffusion limited current produced by oxidation of the reduced form of the redox mediator when the above-stated electrical potential difference is applied.

The meter described above will normally be adapted to apply an algorithm (discussed below) to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby incorporated by reference.

For easy electrical connection of the power source and meter, additional cutout portion 12 (FIGS. 1 through 4), exposing portions of the working and counter electrodes, are preferably provided in the biosensor device.

The biosensor device described above may be used to determine the concentration of an analyte in a fluid sample by performing the following steps:

a) contacting a fluid sample, such as whole blood, with a reagent (described above) that substantially covers surface areas 10 and 20 of working and counter electrodes 4 and 5, respectively;

b) allowing the reaction between the analyte and the oxidized form of the redox mediator to go to completion, as defined herein;

c) subsequently applying a potential difference between the electrodes sufficient to cause diffusion limited electrooxidation of the reduced form of the redox mediator at the surface of the working electrode;

d) thereafter measuring the resulting diffusion limited current; and e) correlating the current measurement to the concentration of analyte in the fluid. (Reaction completion is defined as sufficient reaction between the analyte and the oxidized form of the redox mediator to correlate analyte concentration to diffusion limited current generated by oxidation of the reduced form of the redox mediator at the surface of the working electrode.)

Many analyte-containing fluids may be analyzed. For example, analytes in human body fluids such as whole blood, blood serum, urine and cerebrospinal fluid may be measured. Also, analytes found in fermentation products and in environmental substances, which potentially contain environmental contaminants, may be measured.

When measuring analytes found in human body fluids, especially whole blood, the potential difference applied between the electrodes is preferably no more than about 500 millivolts. When a potential difference above about 500 millivolts is applied between the electrodes, oxidation of the working electrode surface (for palladium) and of some blood components may become intolerable, thereby preventing an accurate and precise correlation of current to analyte concentration. For an assay of glucose in a whole blood sample, wherein the oxidized form of the redox mediator is ferricyanide, a potential difference from about 150 millivolts to about 500 millivolts may be applied between the electrodes to achieve diffusion limited electrooxidation of the reduced form of the redox mediator at the surface of the working electrode. Preferably, about 300 millivolts potential difference is applied between the electrodes.

Current generated from the oxidation of the reduced form of the redox mediator may be measured at any time from about 0.5 seconds to about 30 seconds after the potential difference is applied between the electrodes. At less than about 0.5 seconds, diffusion limited current is difficult to measure due to the charging current. After about 30 seconds, convection becomes significant, thereby interfering with the measurement of a diffusion limited current.

Figure 5:
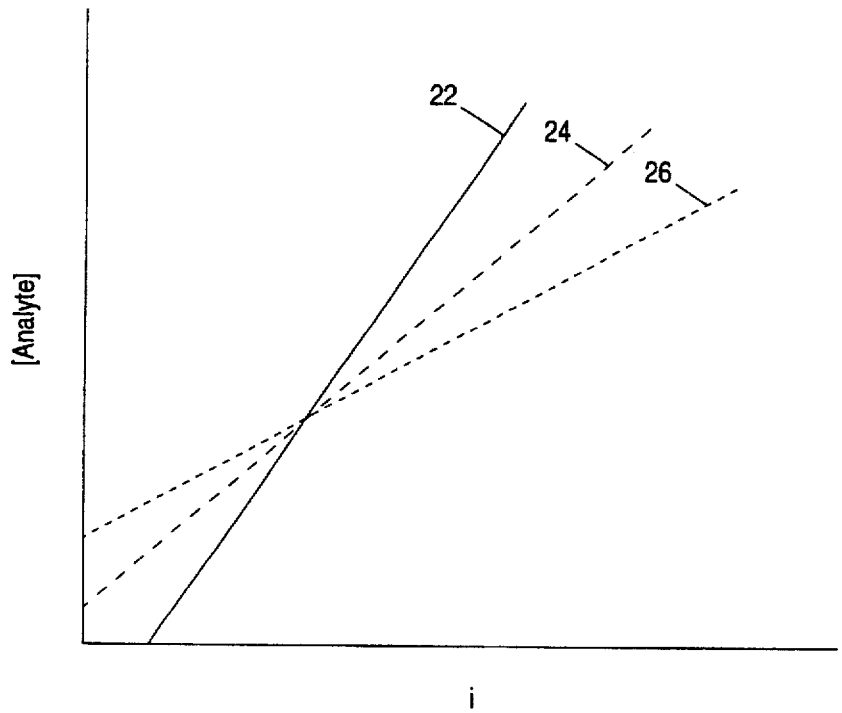
FIG. 5 illustrates hypothetical calibration curves for different lots of biosensor test strips.

The current measured during the assay of an analyte from a fluid sample may be correlated to concentration of the analyte in the sample by application of an algorithm by the current measuring meter. The algorithm may be a simple one, as illustrated by the following example:

$$[\text{Analyte}] = Ci_{7.5} + d$$

wherein [Analyte] represents the concentration of the analyte in the sample (see FIG. 5), $i_{7.5}$ is the current (in microamps) measured at 7.5 seconds after application of the potential difference applied between the electrodes, C is the slope of line 22 (FIG. 5), and d is the axis intercept (FIG. 5).

By making measurements with known concentrations of analyte, calibration curve 22 (FIG. 5) may be constructed. This calibration will be stored in the Read Only Memory (ROM) key of the meter and will be applicable to a particular lot of biosensor test strips. Lines 24 and 26 in FIG. 5 represent other hypothetical calibration curves for two other different lots of biosensor test strips. Calibration for these biosensor lots would generate slightly different values for C and d in the above algorithm.

In analysis of glucose from a sample of human whole blood, 20 µl of whole blood is preferably added to the above-stated glucose reagent. The reaction of glucose and ferricyanide is allowed to go to completion, thereby forming gluconic acid and ferrocyanide. This reaction normally requires a short time, preferably less than about 20 seconds, to go to completion. About twenty seconds after addition of the whole blood sample, a potential difference of about 300 millivolts is applied between the electrodes, thereby oxidizing ferrocyanide to ferricyanide at the surface of the working electrode. Current measurements are made at 0.5 second intervals from 1 second to 7.5 seconds after the potential difference is applied between the electrodes. These current measurements are correlated to the concentration of glucose in the blood sample.

In this example of measuring glucose from a blood sample, current measurements are made at different times (from 1 second to 7.5 seconds after application of the potential difference), rather than at a single fixed time (as described above), and the resulting algorithm is more complex and may be represented by the following equation:

$$[\text{Glucose}] = C_1 i_1 + C_2 i_2 + C_3 i_3 + \ldots C_n i_n + d,$$

wherein $i_1$ is the current measured at the first measurement time (1 second after application of the 300 millivolt potential difference), $i_2$ is the current measured at the second measurement time (1.5 seconds after application of the 300 millivolt potential difference), $i_3$ is the current measured at the third measurement time (2 seconds after application of the 300 millivolt potential difference), $i_n$ is the current measured at the $n^{th}$ measurement time (in this example, at the $14^{th}$ measurement time or 7.5 seconds after application of the 300 millivolt potential difference), $C_1$, $C_2$, $C_3$, and $C_n$ are coefficients derived from a multivariate regression analysis technique, such as Principle Components Analysis or Partial Least Squares, and d is the regression intercept (in glucose concentration units). (A modification of this procedure may be used in the event that calibration curves illustrated by FIG. 5 have considerable curvature.)

Alternatively, the concentration of glucose in the sample being measured may be determined by integrating the curve generated by plotting current, i, versus measurement time over some time interval (for example, from 1 second to 7.5 seconds after application of the 300 millivolt potential difference), thereby obtaining the total charge transferred during the measurement period. The total charge transferred is directly proportional to the concentration of glucose in the sample being measured.

Further, the glucose concentration measurement may be corrected for differences between environmental temperature at the time of actual measurement and the environmental temperature at the time calibration was performed. For example, if the calibration curve for glucose measurement was constructed at an environmental temperature of 23° C., the glucose measurement is corrected by using the following equation:

$$[\text{Glucose}]_{corrected} = [\text{Glucose}]_{measured} \times (1 - K(T - 23^\circ \text{C.})),$$

wherein T is the environmental temperature (in °C.) at the time of the sample measurement and K is a constant derived from the following regression equation:

$$Y = K(T - 23),$$

wherein $$Y = \frac{[\text{Glucose}]_{measured\ at\ 23^\circ C.} - [\text{Glucose}]_{measured\ at\ T^\circ C.}}{[\text{Glucose}]_{measured\ at\ T^\circ C.}}$$

In order to calculate the value of K, each of a multiplicity of glucose concentrations is measured by the meter at various temperatures, T, and at 23° C. (the base case). Next, a linear regression of Y on T−23 is performed. The value of K is the slope of this regression.

The glucose concentration of a sample may be accurately and precisely measured by the present inventive method utilizing the present inventive biosensor. Further, when a sample of human whole blood is measured, error due to hematocrit effect is insignificant in the range of 30–55% hematocrit.

Other examples of enzymes and redox mediators (oxidized form) that may be used in measuring particular analytes by the present invention are listed below in Table 1.

TABLE 1

| ANALYTE | ENZYMES | REDOX MEDIATOR (OXIDIZED FORM) | ADDITIONAL MEDIATOR |
|---------|---------|-------------------------------|---------------------|
| GLUCOSE | GLUCOSE DEHYDROGENASE AND DIAPHORASE | FERRICYANIDE | |
| GLUCOSE | GLUCOSE-DEHYDROGENASE | FERRICYANIDE | |

TABLE 1-continued

| ANALYTE | ENZYMES | REDOX MEDIATOR (OXIDIZED FORM) | ADDITIONAL MEDIATOR |
|---|---|---|---|
| CHOLESTEROL | (QUINOPROTEIN) CHOLESTEROL ESTERASE AND CHOLESTEROL OXIDASE | FERRICYANIDE | 2,6-DIMETHYL-1,4-BENZOQUINONE 2,5-DICHLORO-1,4-BENZOQUINONE OR PHENAZINE ETHOSULFATE |
| HDL CHOLESTEROL | CHOLESTEROL ESTERASE AND CHOLESTEROL OXIDASE | FERRICYANIDE | 2,6-DIMETHYL-1,4-BENZOQUINONE 2,5-DICHLORO-1,4-BENZOQUINONE OR PHENAZINE ETHOSULFATE |
| TRIGLYCERIDES | LIPOPROTEIN LIPASE, GLYCEROL KINASE, AND GLYCEROL-3-PHOSPHATE OXIDASE | FERRICYANIDE OR PHENAZINE ETHOSULFATE | PHENAZINE METHOSULFATE |
| LACTATE | LACTATE OXIDASE | FERRICYANIDE | 2,6-DICHLORO-1,4-BENZOQUINONE |
| LACTATE | LACTATE DEHYDROGENASE AND DIAPHORASE | FERRICYANIDE, PHENAZINE ETHOSULFATE, OR PHENAZINE METHOSULFATE | |
| LACTATE DEHYDROGENASE | DIAPHORASE | FERRICYANIDE, PHENAZINE ETHOSULFATE, OR PHENAZINE METHOSULFATE | |
| PYRUVATE | PYRUVATE OXIDASE | FERRICYANIDE | |
| ALCOHOL | ALCOHOL OXIDASE | PHENYLENEDIAMINE | |
| BILIRUBIN | BILIRUBIN OXIDASE | 1-METHOXY-PHENAZINE METHOSULFATE | |
| URIC ACID | URICASE | FERRICYANIDE | |

In some of the examples shown in Table 1, at least one additional enzyme is used as a reaction catalyst. Also, some of the examples shown in Table 1 may utilize an additional mediator, which facilitates electron transfer to the oxidized form of the redox mediator. The additional mediator may be provided to the reagent in lesser amount than the oxidized form of the redox mediator.

When compared to the preferred embodiment of the closest prior art biosensor test strip, disclosed in Pollmann et al., the present inventive biosensor has the following distinguishing features:

1. reagent well 9 is 30% smaller;
2. when the working and counter electrodes are substantially the same size, the exposed surface area of the counter electrode in the reagent well is less than the exposed surface area of the working electrode in the reagent well;
3. a smaller amount of reagent is needed in the reagent well (4 microliters of reagent vs. 6 microliters of reagent in the preferred embodiment of Pollmann et al.);
4. a smaller spreading mesh is needed; and
5. air vents are included on opposing sides of the reagent well.

A smaller sample volume requirement to properly dose the test strip means fewer underdosing errors will result. This result is especially important for those persons, such as infants and the elderly who have difficulty in obtaining a reasonably sized blood drop after pricking their finger with a lancet. The present inventive strip makes it easier for a current measuring meter to discriminate low sample volume dosing errors. Also, using less reagent per sensor increases production volume for mass producing sensors. Further, providing side air vents near the reagent well reduces the occurrence of air bubbles trapped in the reagent well, which results in fewer testing errors.

The present invention has been disclosed in the above teachings and drawings with sufficient clarity and conciseness to enable one skilled in the art to make and use the invention, to know the best mode for carrying out the invention, and to distinguish it from other inventions and what is old. Many inventions and obvious adaptations of the invention will readily come to mind, and these are intended to be contained within the scope of the invention as claimed herein.

What is claimed is:

1. A device for detecting or measuring the concentration of an analyte, comprising:

a first electrical insulator;

two electrodes only said electrodes consisting of a working electrode and a counter electrode of substantially the same size, made of the same electrically conducting materials and supported on the first electrical insulator;

a second electrical insulator, overlaying the first electrical insulator and the electrodes and including a cutout portion that exposes a smaller surface area of the counter electrode than the working electrode;

a reagent for detecting or measuring the concentration of the analyte, the reagent substantially covering the exposed electrode surfaces in the cutout portion; and a spreading mesh, impregnated with a surfactant, overlaying the cutout portion and affixed to the second electrical insulator, wherein the cutout portion and spreading mesh are of sufficient size and the reagent is in sufficient amount to receive a minimum whole blood sample of about 9 microliters for analyzing the analyte.

2. The device of claim 1, wherein the spreading mesh is affixed to the second substrate by tape having an adhesive on one side and a hole that exposes at least a portion of the spreading mesh and the cutout portion, and wherein the tape also includes at least one slit near the hole, thereby providing at least one air vent.

3. The device of claim 2, wherein the tape includes slits on opposing sides of the hole, thereby providing two air vents.

4. The device of claim 2, wherein the cutout portion is 4 millimeters by 4.2 millimeters.

5. The device of claim 4, wherein the spreading mesh is 6 millimeters by 5.8 millimeters.

6. The device of claim 5, wherein the amount of reagent is 4 microliters before drying.

7. The device of claim 6, wherein the spreading mesh is impregnated with dioctylsodium sulfosuccinate.

8. The device of claim 7, wherein the hole in the tape exposes substantially all of the cutout portion.

9. The device of claim 8, further comprising a current measuring meter in electrical connection with the working and counter electrodes.

10. The device of claim 1, further comprising a current measuring meter in electrical connection with the working and counter electrodes.

* * * * *

UNITED STATES PATENT AND TRADEMARK OFFICE
CERTIFICATE OF CORRECTION

PATENT NO. : 5,762,770
DATED : June 9, 1998
INVENTOR(S) : G. John Pritchard et al.

It is certified that error appears in the above-identified patent and that said Letters Patent is hereby corrected as shown below:

On title page, item [63] Related U.S. Application Data
replace "Continuation-in-part of Ser. No. 198,407, Feb. 22, 1994, Pat. No. 5,508,171"
with --Continuation-in-part of Ser. No. 198,407, Feb. 21, 1994, Pat. No. 5,508,171--.

Signed and Sealed this

Tenth Day of August, 1999

Attest:

Q. TODD DICKINSON

*Attesting Officer*    Acting Commissioner of Patents and Trademarks